United States Patent
Görtler

(10) Patent No.: US 7,030,615 B2
(45) Date of Patent: Apr. 18, 2006

(54) MAGNETIC RESONANCE APPARATUS WITH A POSITIONING UNIT

(75) Inventor: Georg Görtler, Baiersdorf (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 11/083,431

(22) Filed: Mar. 18, 2005

(65) Prior Publication Data

US 2005/0218896 A1 Oct. 6, 2005

(30) Foreign Application Priority Data

Mar. 19, 2004 (DE) .................. 10 2004 013 616

(51) Int. Cl.
*G01V 3/00* (2006.01)

(52) U.S. Cl. .................. 324/318; 600/410

(58) Field of Classification Search ............ 324/318, 324/322, 300; 600/410, 424
See application file for complete search history.

(56) References Cited

U.S. PATENT DOCUMENTS

| | | | | |
|---|---|---|---|---|
| 4,538,289 A | * | 8/1985 | Scheibengraber | ............ 378/20 |
| 4,629,989 A | * | 12/1986 | Riehl et al. | .................. 324/318 |
| 5,178,146 A | * | 1/1993 | Giese | .......................... 600/411 |
| 5,928,148 A | | 7/1999 | Wang et al. | |
| 6,294,915 B1 | * | 9/2001 | Murphy et al. | ............. 324/318 |
| 6,460,206 B1 | | 10/2002 | Blasche et al. | |
| 6,759,847 B1 | | 7/2004 | Brinker et al. | |

FOREIGN PATENT DOCUMENTS

EP 1 382 300 1/2004

* cited by examiner

*Primary Examiner*—Louis Arana
(74) *Attorney, Agent, or Firm*—Schiff Hardin LLP

(57) ABSTRACT

A magnetic resonance apparatus has a positioning unit and a patient bed. The positioning unit can store a number of positions of the patient bed and can automatically position in an imaging volume the associated examination regions established by a marking unit in a diagnostic data acquisition procedure predetermined by a measurement control unit. The positioning unit can detect dimensions of a patient by evaluation of the number of positions of the patient bed and transfer these dimensions to a monitoring module. The monitoring module adapts the RF transmitting power to the patient according to the dimensions.

5 Claims, 1 Drawing Sheet

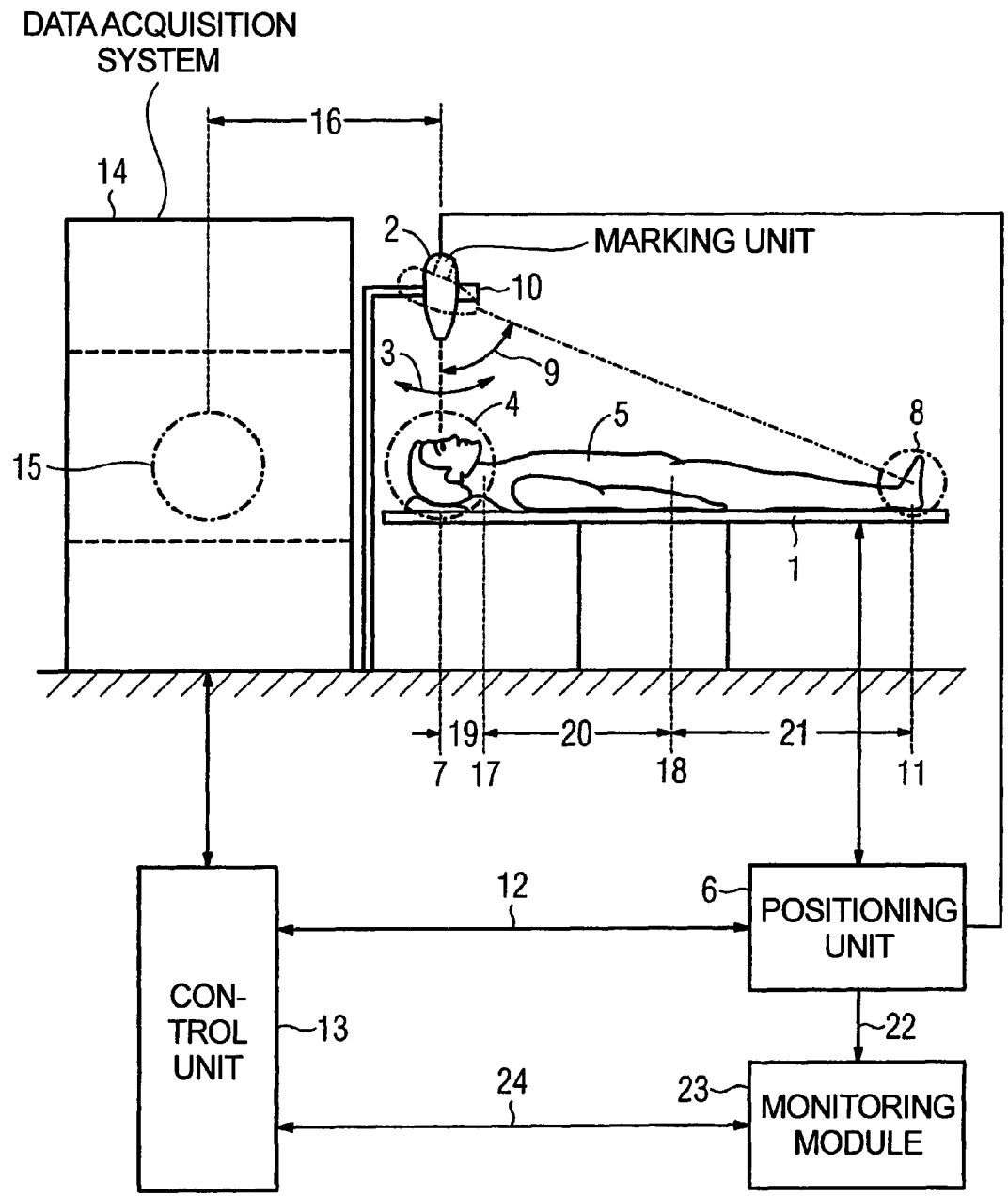

MAGNETIC RESONANCE APPARATUS WITH A POSITIONING UNIT

BACKGROUND OF THE INVENTION

1. Field of the Invention

The present invention concerns a magnetic resonance apparatus of the type having a positioning unit with a marking unit connected thereto, and a movable patient bed, the position of which can be detected and changed by the positioning unit with the marking unit establishing examination regions of an examination subject.

2. Description of the Prior Art

A magnetic resonance apparatus of the above general type is known from German OS 199 47 328. An actuation device serves to establish an examination region of an examination subject who is positioned by movement of the patient bed in an imaging volume of the magnetic resonance apparatus. A disadvantage of this known apparatus is that, in the case of a subsequent examination of a second examination region, the examination subject must be moved out of the magnetic resonance apparatus again in order to establish the second examination region, and the overall duration of the examination is thereby extended.

A method for implementation of an angiography examination using a magnetic resonance apparatus is specified from U.S. Pat. No. 5,928,148 wherein a number of examination regions are examined within one measurement procedure.

A method and an apparatus for positioning of a patient in a medical diagnostic apparatus are described in European Application 1 382 300. The patient is detected by two differently positioned image acquisition devices outside of the diagnostic apparatus. The patient is thereby divided into various body regions by means of image analysis that are available as examination regions.

Since the radiation of RF power into a patient leads to a heating of the irradiated examination region, limit values must be complied with in setting the RF transmitting power in an MR apparatus. The setting for the selected examination region ensues, for example, on the basis of a model in which a geometry of the patient is approximated by a number of cylinders (thus for example one cylinder for each leg, one for the torso and arms, one for the head of the patient) and the RF transmitting power is correspondingly adapted for a selected examination region taking a specific absorption rate (SAR) into account. Differentiation is made only between adults and children. A relatively high uncertainty or imprecision results from this with regard to the maximum compatible RF transmitting power, so that for safety a substantially lower value is used for the data acquisition than the allowable value, which in turn leads to an extended measurement time.

A method for magnetic resonance imaging is known from German OS 101 50 138, in which, before the beginning of the diagnostic data acquisition values for the SAR are determined from patient data and a magnetic resonance pre-measurement. The entire body of the patient is thereby measured to determine the exact body geometry.

SUMMARY OF THE INVENTION

An object of the present invention is to provide a magnetic resonance apparatus of the above type in which the examination procedure is simplified.

The above object is achieved in accordance with the present invention in a magnetic resonance imaging apparatus having a positioning unit and a movable patient bed, wherein the position of the patient bed can be detected and changed by the positioning unit. A marking unit establishes different examination regions of an examination subject on the patient bed. The marking unit is connected to the positioning unit, and the positioning unit determines at least one dimension of the examination subject by evaluating the information regarding the differently positioned examination regions supplied thereto by the marking unit.

At least one dimension of the examination subject is detected by the evaluation of a number of differently positioned examination regions. For example, the size of the head or the length of the legs of a patient can be determined, which then serve for adjustment of measurement parameters in the diagnostic data acquisition process. This offers the advantage that such geometrical information does not have to be acquired via a time-consuming magnetic resonance pre-measurement.

To increase the patient safety and shorten the examination duration, the magnetic resonance apparatus in an embodiment of the invention has a monitoring module that is connected with the positioning unit and the measurement control unit. The monitoring module determines the geometry of the patient from the measured (detected) dimensions, for example from positions of the forehead, neck, hips and feet. The conventionally employed cylinder model thus can be significantly improved, since the geometry is customized to the respective patient. The measurement control unit adjusts the RF transmitting power dependent on the specific absorption rate for the selected examination region. A higher setting of the transmitting power can be used than would ensue on the basis of the cylinder model. A reduction of the measurement time thus results.

In an embodiment, the positioning unit associates the position of the patient bed with the examination region and stores at least two different positions of the patient bed. Due to the storage of a number of bed positions, examinations of various examination regions can be implemented immediately after one another without the patient bed having to be moved out of the magnetic resonance apparatus. The duration of the overall examination is thereby significantly reduced.

In a further version of this embodiment, the positioning unit is connected with a measurement control unit, and the positions of the patient bed stored in the positioning unit are available for a diagnostic data acquisition procedure. During this procedure, the positions are automatically achieved by the positioning unit. This is particularly advantageous in the case of data acquisitions of longer duration, wherein a number of test subjects or test phantoms may be examined multiple times. In accordance with the invention such multiple test scans can ensue immediately after one another and thus for the most part automatically due to the storage of the positions. The positioning unit positions the test subjects in the imaging volume in a sequence desired by the operating personnel.

Preferably the positioning unit automatically positions the patient bed for data acquisition such that the examination region lies in the imaging volume of the magnetic resonance apparatus.

In a further embodiment, the marking unit is pivotable, such that with the patient bed in the same (unchanged) position, differently positioned examination regions can be established on the examination subject. This has the advantage of saving time compared to a magnetic resonance apparatus with a non-pivotable marking unit, since in the latter the examination subject must always be moved by movement of the patient bed.

DESCRIPTION OF THE DRAWINGS

The single FIGURE is a schematic block diagram of a magnetic resonance apparatus with a positioning unit in accordance with the present invention.

DESCRIPTION OF THE PREFERRED EMBODIMENTS

The FIGURE shows the magnetic resonance apparatus with a movable patient bed 1 and a marking unit 2 (shown here as a pivotable laser), the pivot directions of which are indicated by the double arrow 3. The marking unit 2 establishes an examination region 4 on a patient 5. A positioning unit 6 connected with the marking unit 2 detects and stores the position 7 occupied by the patient bed 1 for the examination region 4. A further examination region 8 can be established by pivoting the marking unit 2. The pivot angle 9 necessary for this is determined by a goniometer (protractor) 10 connected with the marking unit 2 and that information is supplied to the positioning unit 6. From the pivot angle 9, the positioning unit 6 calculates the position 11 (that the patient bed 1 must occupy for to the examination region 8) and likewise stores this information. Further examination regions (not shown) can likewise be established and the associated positions stored. The positions 7 and 11 stored in the positioning unit 6 are available to a measurement control unit 13 via a connection 12. The measurement control unit 13 is connected with a measurement system 14 and serves for definition and implementation of a diagnostic data acquisition procedure. Data are acquired from the established examination regions 4 and 8 this procedure. By movement of the patient bed 1, the positioning unit 6 automatically positions the respective examination region 4 or 8 in an imaging volume 15 of the diagnostic data acquisition system 14 at a point in time predetermined by the measurement control unit 13. The marking unit 2 is located at a defined distance 16 from the imaging volume 15. The examination regions 4 and 8 thus are examined in immediate succession without having to move the patient 5 and the patient bed 1 out of the data acquisition system 14 to establish the examination region 8. The data acquisition procedure is thereby simplified and the duration of the procedure is reduced, or more examinations can be implemented per unit of time.

For more efficient dosing of the RF transmitting power set for an examination, the positioning unit 6 can determine a number of dimensions 19, 20 and 21 of the patient 5 by evaluation of a number of positions, here for example positions 7, 11, 17 and 18, and transferring these dimensions to a monitoring module 23 via a connection 22. The monitoring module 23 determines the geometry of the patient 5, for example from the dimensions 19, 20 and 21. Dependent on a specific absorption rate, the monitoring module 23 calculates an allowable maximum value of the RF transmitting power for the respective examination region 4 or 8 and provides this value to the measurement control unit 13 via a connection 24. Thus the RF transmitting power can be set higher than in the known system wherein the geometry of the actual patient 5 is wholly unknown (since it is derived from modules) and the RF transmitting power therefore must be set to a much lower standard value for safety reasons. The duration of the examination is further shortened by the higher RF transmitting power, or more examinations can be implemented per unit of time.

The detection of a number of positions 7, 11, 17 and 18 of the patient bed 1 is also possible with a non-pivotable marking unit (not shown). In this case, the desired examination regions 4 and 8 are positioned (by movement of the patient bed 1) after one another under the non-pivotable marking unit, and the corresponding position of the patient bed 7 and 11 is stored in the positioning unit 6. If the positioning unit 6 is realized as software, this can be integrated into the measurement control unit 13. This has the advantage that magnetic resonance apparatuses already in use that already possess only a non-pivotable marking unit and a measurement control unit 13, and do not have a positioning unit 6 qualified for storage of a plurality of positions 7 and 11 of the patient bed 1, can be upgraded with such a positioning unit 6 via a software update. Time can also be saved and the measurement procedure can be simplified in a simple manner with these magnetic resonance apparatuses.

Although modifications and changes may be suggested by those skilled in the art, it is the intention of the inventor to embody within the patent warranted hereon all changes and modifications as reasonably and properly come within the scope of his contribution to the art.

I claim as my invention:

1. A magnetic resonance apparatus comprising:
   a movable patient bed adapted to receive an examination subject thereon;
   a positioning unit connected to the patient bed for detecting respective positions of the patient bed and for changing the position of the patient bed;
   a marking unit adapted to establish different examination regions of the examination subject;
   said marking unit being connected to said positioning unit and supplying information to said positioning unit regarding the different established examination regions, and said positioning unit detecting at least one dimension of the examination subject by evaluating said information;
   said positioning unit associating respective positions of the patient bed with the respective examination regions established by the marking unit, and storing at least two different positions of said patient bed to allow substantially uninterrupted, successive examination of the examination regions, respectively associated with the stored positions, by successively automatically moving the patient bed between said at least two different positions stored by said positioning unit.

2. A magnetic resonance apparatus as claimed in claim 1 comprising an RF transmitter adapted to transmit RF energy into the examination subject, and a monitoring module connected to said positioning unit and to said RF transmitter, said monitoring module setting the power of the RF energy dependent on said at least one dimension.

3. A magnetic resonance apparatus as claimed in claim 1 comprising a measurement control unit connected to said positioning unit, said positioning unit making said different positions of the patient bed available to the measurement control unit, and said measurement control unit automatically controlling acquisition of diagnostic data from the examination subject on the patient bed dependent on said different positions.

4. A magnetic resonance apparatus as claimed in claim 1 wherein said magnetic resonance apparatus comprises a data acquisition unit having an imaging volume, and wherein said positioning unit positions the respective examination regions established by said marking unit in said imaging volume.

5. A magnetic resonance apparatus as claimed in claim 1 wherein said marking unit is pivotably mounted with respect to said examination subject, and includes a goniometer that detects a pivot angle through which said marking unit pivots between the different examination regions established by the marking unit, said information supplied by the marking unit to the positioning unit comprising said pivot angle.

* * * * *